United States Patent [19]

Hankó

[11] Patent Number: 5,091,194
[45] Date of Patent: Feb. 25, 1992

[54] COSMETIC COMPOSITIONS COMPRISING A NATIVE MINERAL SUBSTANCE FOR THE TREATMENT OF PHLEBECTASIAE AND PROCESS FOR PREPARING SAME

[76] Inventor: László Hankó, Lovag u. 10. III/2, 1066 Budapest, Hungary

[21] Appl. No.: 284,242

[22] Filed: Dec. 14, 1988

[51] Int. Cl.$^5$ .............................. A61K 33/06
[52] U.S. Cl. .................... 424/698; 514/930
[58] Field of Search ............ 424/697, 68, 698

[56] References Cited

U.S. PATENT DOCUMENTS

| | | | |
|---|---|---|---|
| 92,937 | 7/1869 | Butcher | 424/697 |
| 120,879 | 11/1871 | Irwin | 424/697 |
| 357,291 | 3/1921 | Finigan | 424/697 |
| 1,372,496 | 3/1921 | Finigan | 424/697 |
| 3,180,827 | 4/1965 | Martinek et al. | 424/697 |
| 4,613,498 | 9/1986 | Crosby | 424/154 |

OTHER PUBLICATIONS

Medical Dictionary by Dorland's, 26th Ed., p. 1007.

Primary Examiner—Frederick E. Waddell
Assistant Examiner—Celia Chang
Attorney, Agent, or Firm—Keil & Weinkauf

[57] ABSTRACT

The invention relates to cosmetic compositions for the treatment of phlebectasiae, particularly haemorrhoids and phlebectasiae mainly occurring on the lower limbs optionally accompanied with phlebitis, as well as for relieving the phlebalgia thereby induced, with comprises potassium aluminum sulfate and/or one or more hydrates thereof in admixture with one or more cosemtically acceptable carriers, auxiliary and optionally odorizing materials commonly used in the preparation of cosmetics.

The compositions according to the invention preferably contain potassium aluminum sulfate dodecahydrate in an amount of 10 to 90% by weight, most preferably 40 to 70% by weight and are preferably formulated to ointments, creams, lotions or pastes.

1 Claim, No Drawings

COSMETIC COMPOSITIONS COMPRISING A NATIVE MINERAL SUBSTANCE FOR THE TREATMENT OF PHLEBECTASIAE AND PROCESS FOR PREPARING SAME

The invention relates to cosmetic compositions for treating phlebectasiae, particularly haemorrhoids and phlebectasiae mainly occurring on the lower limbs and optionally accompanied with phlebitis as well as for relieving the phlebalgia thereby induced, which comprise a native mineral substance.

According to an other aspect of the invention, there is provided a process for the preparation of these new compositions.

Hereinafter, by the term "haemorrhoids", there are meant the dilatations of the valve-free venour vascular system in the lowest segment of the rectum ("nodi haemorrhoidales").

A long-standing effort of the persons skilled in the art has been aimed to treat the haemorrhoids without any surgical intervention since the cure by a surgical operation requires an extended period of disability to work, it can be carried out only by hospitalization and involves an infection ratio of about 10% being common in the surgery of the colon and rectum [Pharm. Intern. 7, 142 (1986)]. Other problems can also be raised by the surgical intervention in the elderly or in the case of other accompanying diseases.

The therapy of phlebectasiae mainly occurring on the lower limbs is also a frequent task and the surgical intervention may also here be accompanied by the disadvantages discussed above though the risk of infection is lower here.

The formation of both the haemorrhoids and phlebectasiae is highly frequent in all age-groups of the adult population. Thus, an important demand exists on a composition that may topically be used for a long time, provides a relief of phlebalgia and is suitable to ensure the working ability as well as to reduce or alleviate the pathological alterations mentioned above without side-effects.

It is known from the literature to topically use metal salts for relieving complaints caused by haemorrhoids. Basic bismuth gallate, basic bismuth nitrate and basic bismuth iodogallate are e.g. suitable salts for this purpose.

Till now, the metal salts have in every case been used together with plant extracts, oils, corticoids or other drugs [Rote Liste 1983, Main Class 46, Ed. Cantor Aulendorf (Württemberg, German Federal Republic)].

According to the literature alums, i.e. double salts of the general formula $Me^I Me^{III}(SO_4)_2 \cdot 12H_2O$, wherein $Me^I$ stands for potassium, sodium, ammonium, thallium, rubidium or caesium ion and $Me^{III}$ means aluminium, iron, chromium, cobalt or manganese ion, and among them, potassium aluminium sulfate have never been used as active ingredients of one-component compositions for treating phlebectasiae.

Oral compositions commonly induce a number of undesired side effects within even a short period whereas the treatment of haemorrhoids or other phlebectasiae requires a long time. Thus, Venoruton® [chemically O-(β-hydroxyethyl)-rutoside] may e.g. induce rubedo (erythema) and dropsy tumescence of the face after a treatment period of only 6 to 8 days.

The aim of the present invention is to provide a cosmetic composition which is simple and cheap to prepare and contains only a single active ingredient whereby the drawbacks of the known solutions can be eliminated.

Now it has been found that phlebectasiae, particularly the haemorrhoids and phlebectasiae mainly occurring on the lower limbs and optionally accompanied with phlebitis, and the phlebalgia induced thereby can significantly be reduced or alleviated by the topical use of a composition containing exclusively potassium aluminium sulfate or its hydrates (alum) as active ingredient.

According to a preferable embodiment of the present invention, potassium aluminium sulfate dodecahydrate is mixed with a hydrophilic ointment base (carrier) [methylcellulose hydrogel (Hydrogelum methylcellulosi), glycerolic ointment base (Unguentum glycerini), stearin ointment base (Unguentum stearini) or a hydrophilic anionic ointment base (Unguentum hydrophilici anionicum)], which is convenient for preparing cosmetics.

The composition according to the invention may contain also other carriers, auxiliary and odourizing materials commonly used in the preparation of cosmetics.

Suitable carriers, auxiliary and odourizing substances are listed in the Hungarian Pharmacopoea VII, Formulae Normales Ed. VI as well as H. Fiedler: "Lexikon der Hilfstoffe für Pharmazie, Kosmetik . . . Ed. Contor KG. Aulendorf, German Federal Republic, 1971, pages 490 to 494; and "Angewandte Biopharmazie, Ed. Wissenschaftliche Verlagges. Stuttgart, German Federal Republic, 1973, Chapters 26 and 28.

The compositions according to the invention preferably contain potassium aluminum sulfate dodecahydrate in an amount of 10 to 90% by weight, most preferably 40 to 70% by weight.

According to our observations, when the varicose veins to be treated were smeared thrice in a day by using the ointment according to the invention, i.e. an ointment containing 70% by weight of potassium aluminum sulfate, the pain (phlebalgia), pruritus and inflammation were strongly reduced and then alleviated after 1 to 3 treatments; after a treatment lasting 3 to 20 days, the working ability was restored (with a complete painlessness); whereas the phlebectasiae (vein varicosities were eliminated and the protruding vein vessels retreated to their original place after further treatment. These observations were made on 18 patients with an age between 20 and 70 years.

The invention also relates to a method for treating phlebectasiae, particularly haemorrhoids and phlebectasiae mainly occurring on the lower limbs as well as for relieving phlebalgia. This method can be excellently used with persons working in standing position.

The compositions according to the invention are illustrated in detail by the following non-limiting Examples.

EXAMPLE 1

1400 g of crystalline potassium aluminum sulfate dodecahydrate are powdered and mixed with 600 g of glycerolic ointment base (Unguentum glycerini). The stirring is continued until obtaining a homogeneous mass which is then filled in 50 g portions into tubes.

EXAMPLE 2

After mixing 1400 g of potassium aluminum sulfate dodecahydrate with 600 g of a glycerolic ointment base as described in Example 1, 60 ml of chamomile oil are mixed to and the ointment thus obtained is filled into glass jars.

EXAMPLE 3

210 g of potassium aluminum sulfate dodecahydrate are stirred with 90 g of a glycerolic ointment base and 2 g of menthol to a homogeneous mass and then filled into tubes.

EXAMPLE 4

100 g of crystalline potassium aluminum sulfate dodecahydrate are stirred with 900 g of an emulsifying aqueous ointment base (Unguentum emulsificans aquosum) and 7 g of menthol to a homogeneous mixture and then filled in 50 g portions into tubes. The ointment thus obtained is suitable for treating mainly phlebectasiae.

EXAMPLE 5

500 g of cocoa butter are transformed together with 500 g of potassium aluminum sulfate dodecahydrate to a homogeneous cream and filled in 50 g portions into tubes. The cream thus obtained is useful for treating mainly haemorrhoids.

EXAMPLES 6

The process described in Example 4 is followed, except that 900 g of a hydrophilic ointment USP (Unguentum hydrophilicum USP) are used as ointment base.

I claim:

1. A method for treating phlebitis occurring in the lower limb of a human, which comprises topically applying to the affected area a composition consisting essentially of a pharmaceutically acceptable carrier and an amount of potassium aluminum sulfate or a hydrate thereof effective to alleviate the phlebitis.

* * * * *